(12) United States Patent
Fridman et al.

(10) Patent No.: US 7,973,207 B2
(45) Date of Patent: Jul. 5, 2011

(54) ENDOTHERMIC HYDROCARBON CONVERSION PROCESS

(75) Inventors: Vladimir Fridman, Louisville, KY (US); Michael A. Urbancic, Louisville, KY (US)

(73) Assignee: Sud-Chemie Inc., Louisville, KY (US)

(*) Notice: Subject to any disclaimer, the term of this patent is extended or adjusted under 35 U.S.C. 154(b) by 788 days.

(21) Appl. No.: 11/873,367

(22) Filed: Oct. 16, 2007

(65) Prior Publication Data

US 2008/0097134 A1 Apr. 24, 2008

Related U.S. Application Data

(63) Continuation-in-part of application No. 11/218,949, filed on Sep. 2, 2005, now Pat. No. 7,622,623.

(51) Int. Cl.
| | |
|---|---|
| C07C 2/76 | (2006.01) |
| C07C 2/78 | (2006.01) |
| C07C 5/08 | (2006.01) |
| C07C 11/00 | (2006.01) |
| C07C 5/09 | (2006.01) |
| C07C 5/327 | (2006.01) |
| B01J 20/00 | (2006.01) |
| B01J 23/00 | (2006.01) |

(52) U.S. Cl. ........ 585/602; 585/616; 585/617; 585/629; 502/106; 502/300; 502/305; 502/306; 502/307; 502/318; 502/320; 502/415

(58) Field of Classification Search .......... 502/102–106, 502/300, 305–307, 318, 320, 329, 353, 415; 585/602, 616, 617, 629
See application file for complete search history.

(56) References Cited

U.S. PATENT DOCUMENTS

| | | | |
|---|---|---|---|
| 2,399,678 A | 5/1946 | Houdry |
| 2,419,997 A | 5/1947 | Houdry |
| 2,423,029 A | 6/1947 | Houdry |
| 2,423,835 A | 7/1947 | Houdry |
| 3,488,402 A | 1/1970 | Michales et al. |
| 3,665,049 A | 5/1972 | Cornelius |
| 3,754,051 A | 8/1973 | Suzukawa |
| 3,798,178 A | 3/1974 | Soderquist |
| 3,905,917 A | 9/1975 | Nishino |
| 4,065,406 A | 12/1977 | Nishino |
| 4,149,996 A | 4/1979 | Manning |
| 4,418,237 A | 11/1983 | Imai |
| 4,435,607 A | 3/1984 | Imai |
| 4,746,643 A | 5/1988 | Buonomo |
| 4,788,371 A | 11/1988 | Imai |
| 5,108,973 A | 4/1992 | Sakek |
| 5,510,557 A | 4/1996 | Gartside |
| 5,545,787 A | 8/1996 | Cooper |
| 5,827,496 A | 10/1998 | Lyon |

(Continued)

FOREIGN PATENT DOCUMENTS

JP 1086944 2/1986

(Continued)

*Primary Examiner* — Jerry Lorengo
*Assistant Examiner* — Jennifer A Smith
(74) *Attorney, Agent, or Firm* — Scott R. Cox

(57) ABSTRACT

The present invention is an improved cyclic, endothermic hydrocarbon conversion process and a catalyst bed system for accomplishing the same. Specifically, the improved process comprises reacting a hydrocarbon with a multi-component catalyst bed in such a manner that the temperature within the catalyst bed remains within controlled temperature ranges throughout all stages of the process. The multi-component catalyst bed comprises a reaction-specific catalyst physically mixed with a heat-generating material.

16 Claims, 1 Drawing Sheet

U.S. PATENT DOCUMENTS

| | | |
|---|---|---|
| 6,326,523 B1 | 12/2001 | Stahl |
| 6,891,138 B2 | 5/2005 | Dalton |
| 7,067,455 B2 | 6/2006 | Chen |
| 7,074,977 B2 | 7/2006 | Rapier |
| 7,192,987 B2 | 3/2007 | Van Egmond |
| 7,196,239 B2 | 3/2007 | Van Egmond |
| 7,199,276 B2 | 4/2007 | Sher |
| 2004/0092391 A1 * | 5/2004 | Rokicki et al. ............... 502/308 |
| 2004/0192391 A1 | 9/2004 | Nagai |
| 2007/0054801 A1 | 3/2007 | Fridman et al. |

FOREIGN PATENT DOCUMENTS

| | | |
|---|---|---|
| RU | 2157279 | 10/2000 |
| RU | 2254162 | 6/2005 |
| WO | 02068119 | 9/2002 |
| WO | 03013715 | 2/2003 |

* cited by examiner

ENDOTHERMIC HYDROCARBON CONVERSION PROCESS

CROSS REFERENCE TO RELATED APPLICATIONS

This application is a continuation-in-part of application Ser. No. 11/218,949, filed Sep. 2, 2005, now U.S. Pat. No. 7,622,623, which is incorporated herein in its entirety by reference.

BACKGROUND

The present invention relates to an improved cyclic, endothermic hydrocarbon conversion process and to a catalyst bed system for accomplishing the same. Specifically, the improved process comprises contacting a hydrocarbon feedstock with a multi-component catalyst bed, wherein the catalyst bed comprises a first component that is a catalyst specifically designed to convert the hydrocarbon feed to a predetermined product or product mix, and a second component that generates heat after being exposed to reducing and/or to oxidizing reaction conditions.

Several endothermic hydrocarbon conversion processes are utilized in commercial operations. These processes include the Houdry cyclic fixed bed dehydrogenation process, the fluid bed paraffin dehydrogenation process, the fluid bed ethylbenzene dehydrogenation process, and fluid bed catalytic cracking process, among others. Because these processes are endothermic, heat must be consumed from the surroundings in order for the hydrocarbon conversion reaction to occur. In each of these processes, at least one reaction is promoted by contacting a hydrocarbon feed with a catalyst. Further, in each of these processes there is at least one reducing and/or oxidizing reaction that regenerates the catalyst. The heat needed for the endothermic reactions to occur is provided in part by combustion of coke and other undesirable side products that deposit on the catalyst during the conversion process. This combustion takes place during the regeneration process. However, additional heat is normally needed and this is provided by hot air or steam that is fed into the catalyst bed from external sources between the hydrocarbon conversion cycles.

As an example, in the typical Houdry dehydrogenation process as taught in U.S. Pat. No. 2,419,997, an aliphatic hydrocarbon passes through a dehydrogenation catalyst bed. As the aliphatic hydrocarbon passes through the catalyst bed, the hydrocarbon is dehydrogenated to its complementary olefin. The olefin is then flushed from the catalyst bed, the catalyst is regenerated and reduced, and the cycle is repeated. This dehydrogenation reaction is highly endothermic. Therefore, during the dehydrogenation step, the temperature near the inlet of the catalyst bed (where the aliphatic hydrocarbon initially enters the catalyst bed) can decrease by as much as 100° C. This decrease in temperature causes a decrease in hydrocarbon conversion. In addition, during the dehydrogenation step, it is common for coke to form and deposit on the catalyst, further reducing the activity of the catalyst.

In order to reheat the catalyst bed and to remove the coke that has deposited on the catalyst, the reactor is purged of hydrocarbon and then undergoes a regeneration step with air heated to temperatures of up to 700° C. Heat is provided to the bed by the hot air that passes through the bed and also by the combustion of the coke deposits on the catalyst. Reduction of the catalyst, with a reducing gas such as hydrogen, prior to the dehydrogenation step also provides some heat. During regeneration, the hot air flows from the inlet of the catalyst bed to the outlet. This regeneration cycle is normally relatively short, so there is a tendency for the inlet of the bed to be significantly hotter than the outlet of the bed, but because of the timing between cycles in the Houdry dehydrogenation process, the catalyst bed does not have time to equilibrate thermally. Thus, the outlet section of the bed remains cooler than the inlet section of the bed as aliphatic hydrocarbon is again fed into the reactor. The high temperature at the inlet of the bed tends to cause the formation of undesirable by-products and thus lowers selectivity and yield of the desired olefin. On the other hand, the lower temperature at the outlet of the bed does not allow full utilization of the catalyst and thus the olefin yield is lower than would be otherwise expected or desired. Also, because the coke distribution in the catalyst bed is not an independently controlled parameter, the heat distribution is also not easily controllable within the bed. Each of these factors affects the resulting catalyst bed temperature profile and makes control of the temperature profile in the bed difficult.

In U.S. Pat. No. 2,423,835, Houdry teaches that the catalyst bed temperature may be controlled within a temperature range suitable for the reactions without requiring an extraneous heating or cooling fluid to be circulated through or around the reaction chamber by including within the catalyst bed "inert" material capable of absorbing or storing up heat which can subsequently be released as desired or required. In commercial practice for fixed bed reactors, this is typically achieved by using a physical mixture of a dehydrogenation catalyst and a granular, alpha-alumina "inert" material as the catalyst bed. Although the addition of the inert material provides a reversible heat sink for the process, and helps stabilize the overall temperature swings in the reactor, the inert is not capable of providing extra heat for the process nor can it produce heat during any stage of the process. Hence, an external heat source is still required even with the combined use of the catalyst and the inert.

The challenge is to identify a commercially feasible means for controlling the temperature profile within the catalyst bed of an endothermic process. Ideally, any such means will allow for heat addition to predetermined sections of the catalyst bed without using a catalytically active material that produces large quantities of unwanted side products.

SUMMARY OF THE INVENTION

The present invention is an improved endothermic hydrocarbon conversion process and a catalyst bed system for accomplishing the same. Specifically, the improved process comprises reacting a hydrocarbon with a multi-component catalyst bed in such a manner that the temperature within the catalyst bed remains within controlled temperature ranges throughout all stages of the process. The multi-component catalyst bed comprises a reaction-specific catalyst physically mixed with a heat-generating material. Optionally, an inert material, as is known in the art, may be further physically combined with the catalyst and the heat-generating material. The heat-generating material adds heat to the catalyst bed in such a manner that the bed at the outlet section is maintained at a high enough temperature to efficiently convert the hydrocarbon to the olefin. In an exemplary embodiment, the process is a Houdry dehydrogenation process, the reaction-specific catalyst is a conventional chromium-based dehydrogenation catalyst, and the heat-generating material is copper oxide supported on a calcium-aluminate support, and an optionally present inert is alpha-alumina.

Catofin® Standard catalyst and 45 vol. % alpha-alumina during the conversion of propane to propylene.

Figure 2:
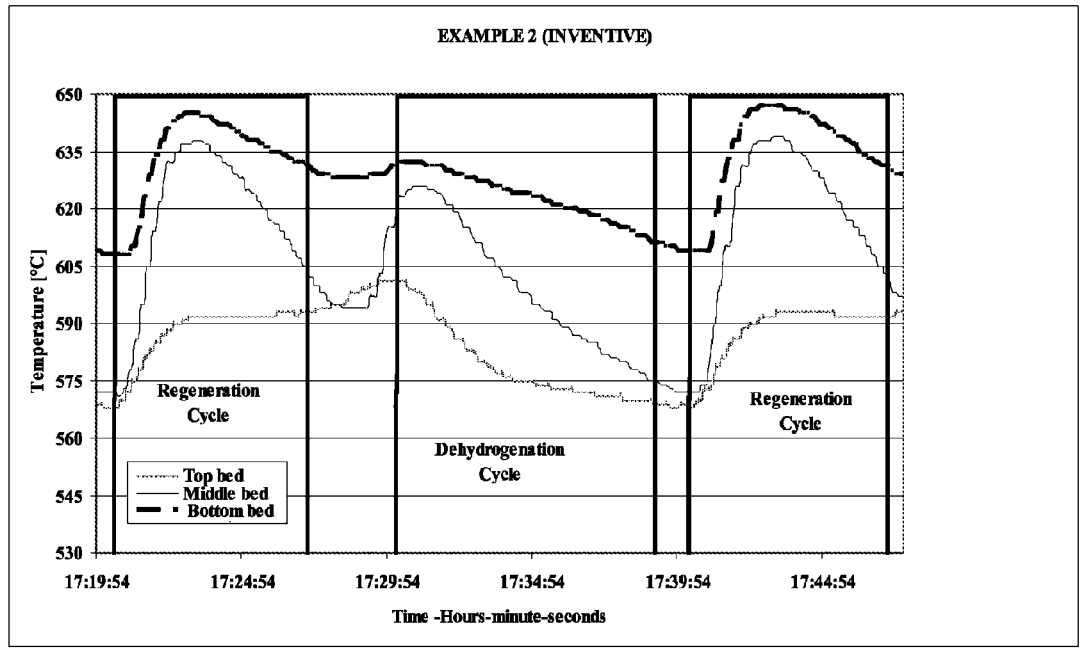

FIG. 2 is a graphical representation of the temperature profile within an adiabatic reactor during the conversion of propane to propylene wherein the reactor is loaded in three sections divided as approximately 35% outlet, 30% middle and 35% inlet, and wherein the outlet section and the inlet section of the bed comprise 55 vol. % Catofin® Standard catalyst and 45 vol. % alpha-alumina and the middle section of the bed comprises 55 vol. % Catofin® Standard catalyst and 45 vol. % copper oxide on a calcium-aluminate support.

DETAILED DESCRIPTION OF THE PREFERRED EMBODIMENT

The improved process of the present invention is intended for use in any cyclic, endothermic hydrocarbon conversion process, whether in fixed bed or fluid bed applications. The improved process requires that a hydrocarbon feedstock contacts a multi-component catalyst bed in order to effect an endothermic hydrocarbon conversion and that the catalyst bed then be exposed to either oxidizing and/or reducing conditions. The catalyst bed comprises a catalytic first component and a heat-generating second component. The catalytic first component must be a catalyst specifically designed to convert the hydrocarbon feed to a predetermined product or product mix via an endothermic reaction. The heat-generating second component must be a material that generates heat after being exposed to reducing and/or to oxidizing reaction conditions but that is relatively inert to the hydrocarbon feedstock with respect to undesirable side reactions, such as coke formation. Optionally, the heat-generating component may catalyze the conversion of the hydrocarbon to the desired product or product mix. The multi-component catalyst bed may further optionally include an inert material, as is known in the art, for use in catalyst beds.

For the purposes of describing the invention in detail, improvements to the Houdry cyclic dehydrogenation process using a fixed bed reactor will be used as an embodiment. However, it is to be understood that the invention may be modified without deviating from the scope of the invention to function in the inventive manner in other cyclic, endothermic hydrocarbon conversion processes, such as without limitation, fluid bed paraffin dehydrogenation processes and fluid bed ethylbenzene dehydrogenation processes.

The equipment used for the Houdry cyclic dehydrogenation process includes an adiabatic reactor containing a fixed catalyst bed wherein the bed defines an inlet section and an outlet section. The catalyst bed comprises the catalytic first component and the heat-generating second component. Optionally, as is known in the art, an inert material may also be added to the catalyst bed.

For the purposes of describing the invention, but without intending any limitation through such description, the fixed catalyst bed is essentially divided into three approximately equal parts—the inlet section of bed, a middle section of bed, the outlet section of bed. Unless otherwise specified, for any examples presented herein, the catalytic first component combined with an inert material is used in the inlet and outlet sections of the bed; and the catalytic first component combined with the heat-generating second component, and used with or without an inert material, is used in the middle section of the bed. While convenient for description purposes, it should be understood that several variations in the component combinations are possible with the fixed catalyst bed. For example, when the bed is divided into three sections, the bed may be divided such that (a) each of the three sections is of approximately equal volume, or (b) the middle section may be larger than about one-third the total catalyst volume, or (c) the middle section may be smaller than about one-third the total catalyst volume, or (d) the inlet section and the outlet section may be of unequal volumes, or (e) any combination thereof. Further, it is not necessary that the bed be divided into three sections. For example, the dehydrogenation catalyst may be mixed with the heat-generating material and used with or without additional inert material and the mixture may then be loaded into the reactor with no sectioning. Alternatively, the catalyst bed may be divided into two sections with the dehydrogenation catalyst combined with an inert either in an inlet section or in an outlet section, and the dehydrogenation catalyst combined with the heat-generating material and used with or without additional inert material in either the outlet section or inlet section, respectively. In some situations, it may also be beneficial to divide the catalyst bed into more than three sections with layers of dehydrogenation catalyst optionally combined with inert material alternating with layers of dehydrogenation catalyst combined with heat-generating material used with or without additional inert material.

As is known in the art, however, there are some practical limitations to the catalyst bed orientations. For example, it is known that if a section of a catalyst bed becomes too hot, there is a risk of reaction runaway. Thus, the user would be well-advised to be aware of the temperature profile for the reaction of interest without the addition of the heat-generating material and to use this as a guide to determine where the heat-generating material would be most effective within the catalyst bed. Further, the amount of heat-generating material added to the catalyst bed at any particular area should be determined by the amount of heat that must be replaced in the process throughout the catalyst bed. That is, the heat generated by the heat-generating material must be less than the heat consumed by the principal reaction in each part of the catalyst bed. Improperly concentrating the heat-generating material in one section of the bed could result in a temperature profile that shows greater temperature deviations than the temperature profile of the process without the use of the heat-generating material.

The example process generally follows the typical Houdry dehydrogenation process as described in U.S. Pat. No. 2,419, 997. The Houdry process includes a series of stages wherein the catalyst bed is evacuated, reduced with hydrogen and evacuated, then an aliphatic hydrocarbon is introduced and dehydrogenated, then the catalyst bed is steam purged and regenerated, and the cycle is repeated starting with the reduction stage.

In the inventive process, the catalyst bed is evacuated and reduced with a reducing gas such as hydrogen. During this stage, the heat-generating second component in the reactor bed generates additional heat that passes into the catalytic first component of the reactor bed. Then an aliphatic hydrocarbon is fed into the catalyst bed and is dehydrogenated upon contact with the catalytic first component of the reactor bed. Because the catalytic first component of the bed has been essentially pre-heated by the heat-generating second component, the catalytic first component demonstrates improved conversion relative to a reactor bed that does not include the heat-generating second component. The catalyst bed is then steam purged and regenerated, and the cycle is repeated starting with the reduction stage. During the regeneration step, the heat-generating second component may also generate additional heat. In a preferred embodiment, the heat-generating second component is selected such that no significant negative effect on selectivity for the hydrocarbon conversion reaction is observed.

In the inventive dehydrogenation process, the catalytic first component may be any catalyst designed for use in dehydrogenation reactions, such as a Catofin® Standard catalyst available from Süd-Chemie Inc., Louisville, Ky. Catofin® Standard catalyst is a chromium oxide dehydrogenation catalyst, manufactured on an alumina support, comprising from about 17 wt % to about 22 wt % $Cr_2O_3$.

The heat-generating second component must be a material that can generate heat after being exposed to reducing and/or to oxidizing reaction conditions but that is relatively inert with respect to hydrocarbon conversion to undesirable products or to undesirable side reactions. The heat-generating second component comprises a metal selected from the group consisting of copper, chromium, molybdenum, vanadium, cerium, yttrium, scandium, tungsten, manganese, iron, cobalt, nickel, silver, bismuth and combinations thereof. Exemplary carriers for the heat-generating second component include, but are not limited to, various aluminum oxides or hydroxides such as aluminum trihydroxide, boehmite, pseudo-boehmite, gibbsite, bayerite, transition aluminas or alpha-alumina, silica/alumina, silica, silicates, aluminates such as calcium aluminate or barium hexyluminate, calcined hydrotalcites, zeolites, zinc oxide, chromium oxides, magnesium oxides and combinations thereof. Optionally, the heat-generating second component may further comprise a promoter, such as an alkali, an alkaline earth metal, lithium, sodium, potassium, rubidium, cesium, beryllium, magnesium, calcium, strontium, zirconium, barium and a combination thereof.

The metal comprises from about 1 wt % to about 100 wt % of the total heat-generating second component weight. In a more preferred embodiment, the metal comprises from about 2 wt % to about 40 wt % of the total second component weight; and in a most preferred embodiment, the amount of metal is from about 5 wt % to about 10 wt % of the total second component weight.

The heat-generating second component is prepared by essentially the same methods known in the art for preparing a supported catalyst. For example, the heat-generating second component may be prepared by precipitation of the carrier with the metal, or by impregnation of the second carrier with the metal. Promoters may further be added with the metal, or may be otherwise added to the second component via methods known in the art for the addition of promoters.

Before loading into the reactor the catalytic first component may be physically mixed with an inert material, as is known in the art. This inert material may be any material, or combination of materials, that is catalytically inactive with respect to undesirable side reactions and that has a high density and high heat capacity, but that is not capable of producing heat during any stage of the process. A commonly used inert material is a granular, alpha-alumina material of similar particle size to the supported catalytic first component. Further as is known in the art, the volume ratio between the inert material and the catalytic first component depends on a number of factors including, but not limited to, the type of hydrocarbon feed being used in the dehydrogenation process. In the present application, no particular volume ratio is prescribed, but rather the user may adjust the ratio as appropriate for the intended use.

For a fixed bed application, the catalyst bed is prepared by physically mixing the catalytic first component and/or the inert material and/or the heat-generating second component. Initially, the desired amount of catalytic first component and the desired bed configuration is defined. The catalytic first component is then divided into the defined quantities and is physically mixed with either the heat-generating second component or with the inert material or with a combination of the heat-generating second component and the inert material. The mixtures are then loaded into the reactor per the desired bed configuration. The heat-generating second component does not affect the amount of catalyst added nor the relative ratio of catalyst to inert material in the resultant catalyst bed.

The catalyst bed system of the present development also may be used in moving fluid bed operations. In an exemplary fluid bed operation, presented for example only and not intended to be limiting, a dehydrogenation processing system has two parallel adiabatic reactors—a first reactor for dehydrogenation reactions and a second reactor for regeneration. The system operates by loading a dehydrogenation catalyst into the first reactor, providing a residence time of about 15 minutes in the first reactor, then moving the loaded catalyst to the second reactor and providing a residence time of about 15 minutes, and then returning the catalyst to the first reactor and continuing the alternating reactor process. In the regeneration reactor the catalyst is treated at 650° C. in air and is reheated by heat of burning coke that was formed during the dehydrogenation step and by the hot air. As the catalyst is moved from the second reactor back to the first reactor, it is subjected to a reducing environment to prepare the catalyst for use in another dehydrogenation reaction.

In the moving fluid bed operation, the dehydrogenation catalyst typically is not mixed with an inert material, and relatively broad temperature swings are observed as the process cycles through the various stages. However, using the inventive method, the dehydrogenation catalyst is combined with the heat-generating second material and is uniformly loaded into the dehydrogenation reactor. The catalyst plus heat-generating material is then moved to the regeneration reactor where coke is burned off the reaction-specific catalyst. As the catalyst plus heat-generating material returns to the dehydrogenation reactor, the heat-generating material is activated by the reducing environment and adds sufficient heat to the catalyst bed to increase the amount of hydrocarbon conversion as compared to the conversion level in fluid bed catalyst loads that do not include a heat-generating material.

The following are representative examples of the present invention for making and using the catalytic first component and the heat-generating second component in fluid and fixed bed applications. These examples are presented to further explain the invention and are not intended, or to be taken, to limit the scope of the invention.

Material Preparation

EXAMPLE A

A catalytic first component sold under the tradename Catofin® Standard catalyst and available from Süd-Chemie Inc., Louisville, Ky. is used in a commercial dehydrogenation unit for 180 days. The catalyst has a chromium oxide concentration of about 19 wt % based on total catalyst weight.

EXAMPLE B

A chromia/potassium oxide/gamma-alumina dehydrogenation catalyst having a mean particle size of about 75 µm is prepared. The catalyst has a chromium oxide concentration of 17.5 wt % and a potassium oxide concentration of 1.0 wt % based on total catalyst weight.

EXAMPLE C

A heat-generating second component is prepared according to the invention as follows: an alpha-alumina support is impregnated with a saturated solution of copper nitrate, the impregnated support is then dried at 120° C. followed by calcining at 750° C. in an air-steam atmosphere. The heat-generating second component has a CuO concentration of about 11 wt % based on the weight of the second component.

EXAMPLE D

A heat-generating second component is prepared according to the invention as follows: calcium-aluminate (Ca-aluminate) is pelletized as approximately 3.5 mm pellets, the Ca-aluminate is then calcined at about 1300° C. for about 10 hours, the calcined material is then impregnated with a saturated solution of copper nitrate and manganese nitrate, and the impregnated material is dried for about 4 hours at about 250° C. followed by calcining at from about 500° C. for about 5 hours. The heat-generating second component has a CuO concentration of about 11 wt % and a $MnO_2$ concentration of about 0.5 wt % based on the weight of the second component.

EXAMPLE E

A heat-generating second component is prepared according to the invention as follows: boehmite alumina is mixed with calcium oxide and the mixture is spherudized to make 6 mm diameter pellets which are dried at 120° C. and then calcined at 1300° C., the pellets having a final CaO content of 18 wt %. The calcined pelletized material is impregnated with a saturated solution of copper nitrate and manganese nitrate, and the impregnated material is dried at about 250° C. followed by calcining in air at 1400° C. The heat-generating second component has a CuO concentration of about 11 wt % and a $MnO_2$ concentration of about 0.5 wt % based on the weight of the second component.

EXAMPLE F

A heat-generating second component is prepared according to the invention as follows: alumina trihydrate (gibbsite) is pelletized as approximately 5 mm pellets, the gibbsite is then calcined at about 550° C. for about 4 hours, the calcined material is then impregnated with a saturated solution of copper nitrate, and the impregnated material is dried for about 4 hours at about 250° C. followed by calcining at from about 500° C. to 1400° C. The heat-generating second component has a CuO concentration of about 11 wt % and a $MnO_2$ concentration of about 0.5 wt % based on the weight of the second component.

EXAMPLE G

A heat-generating second component is prepared according to the invention as follows: a gamma-alumina support having a mean particle size of about 75 μm is impregnated with a saturated solution of copper nitrate and manganese nitrate, the impregnated material is then dried at about 250° C. followed by calcining in air at 750° C. The heat-generating second component has a CuO concentration of about 8 wt % and a $MnO_2$ concentration of about 0.4 wt % based on the weight of the second component.

EXAMPLE H

The catalytic first component of Example A is physically mixed with an inert, alpha-alumina, in a 55 vol. % first component/45 vol. % alpha-alumina ratio.

EXAMPLE I

The catalytic first component of Example A is physically mixed with the heat-generating second component of Example E in a 55 vol. % first component/45 vol. % heat-generating component ratio.

EXAMPLE J

The catalytic first component of Example B is physically mixed with the heat-generating component of Example G in an 80 vol. % first component/20 vol. % heat-generating component ratio.

EXAMPLE K

The catalytic first component of fresh Catofin® Standard catalyst is physically mixed with the heat-generating second component of Example F in a 55 vol. % first component/45 vol. % heat-generating component ratio.

EXAMPLE L

The catalytic first component of fresh Catofin® Standard catalyst is impregnated with a saturated solution of copper nitrate, and the copper-impregnated chromium-based catalyst is dried at 120° C. and calcined at 750° C. in an air-steam atmosphere. The copper-impregnated catalyst has a chromium oxide concentration of 17.5 wt % and a copper oxide concentration of 11 wt % based on total catalyst weight.

EXAMPLE M

A prior art catalyst is prepared according to Example 1 of WO 02/068,119. The catalyst is prepared by combining 860 g boehmite alumina, 800 g copper hydroxide carbonate, 120 g barium acetate, 100 g $CrO_3$, 700 g $NH_4HCO_3$, and 250 g deionized water in an Eirich mixer. Particles approximately 3 mm in diameter are formed and dried at 120° C. for 8 hours and calcined in oven at 650° C. for 10 hours. The copper-impregnated catalyst has a chromium oxide concentration of 45 wt % and a copper oxide concentration of 40 wt % based on total catalyst weight.

EXAMPLE N

A prior art catalyst is prepared according to Example 1 of U.S. Pat. No. 5,108,973. The catalyst is prepared by blending 763.8 g of alumina sol (containing 7.51% $Al_2O_3$) and 89.3 g of chromium nitrate hexahydrate in a one-gallon blender until the solids are dissolved. Copper nitrate hexahydrate (116.3 g) is dissolved in 200 ml DI water and added to the blender. Then 61.8 mol of boric acid is dissolved in 350 ml warm deionized water and also added to the blender. The mixture is blended for an additional two minutes until the mixture becomes homogeneous and a deep blue color. Then 700 ml of 20% ammonium hydroxide in methanol solution is added to form a thick gel. The gel is placed on plastic trays for drying and is dried for 4 hour at 180° C., and then calcined by the following sequence: 25° C. for 2 hours, 175° C. for 12 hours, 400° C. for 4 hours, 830° C. for 8 hours, 830° C. for 4 hours, 250° C. for 3 hour and then cooled to RT. The calcined material is tabletted to form particles of 3 mm diameter. The copper-impregnated catalyst has a chromium oxide concentration of 19 wt % and a copper oxide concentration of 25 wt % based on total catalyst weight.

Performance Testing

EXAMPLES 1 and 2

Catalyst combinations are tested for the conversion of propane to propylene in a down-flow adiabatic reactor having a catalyst bed volume of approximately 3600 cc. Propane and air are fed into the reactor through an inlet and propylene is recovered from an outlet. The process is carried out at a liquid hourly space velocity of 1.0, with propane temperatures from 540° C. to 600° C. and air temperatures from 540° C. to 620° C., and at an air to hydrocarbon ratio of 7.1 wt/wt. The reactor is operated in the cyclic mode common for Houdry processes with the cycle times of 60 seconds for reduction by hydrogen, 540 seconds for dehydrogenation, 60 seconds for evacuation, 540 seconds for regeneration-reheat-oxidation, and 60 seconds for evacuation. The reactor is operated at a pressure of 0.5 atm during the dehydrogenation step of the cycle and at atmospheric pressure during the regeneration step of the cycle. The cyclic operation is repeated 300 times.

EXAMPLE 1

Reactor Loading—100 vol. % catalyst combination of Example H.

EXAMPLE 2

Reactor Loading—approximately 35 vol. % of material from Example H is loaded near the outlet of the down-flow adiabatic reactor, then approximately 30 vol. % of material from Example I is loaded into a middle section of the reactor, then approximately 35 vol. % of material from Example H is loaded near the inlet.

TABLE 1

Performance characteristics of catalysts in propane dehydrogenation (Adiabatic Fixed Bed Reactor)

|  | Example | |
| --- | --- | --- |
|  | 1 (prior art) | 2 (inventive) |
| Bed Components (vol %) | 100% Ex. H | 35% Ex. H/30% Ex. I/ 35% Ex. H |
| Heat-Generating Component | none | copper oxide/ manganese oxide/ Ca-aluminate |
| Inlet Propane T = 540° C. | | |
| Propane Conversion: [wt %] | 18.3 | 45.1 |
| Propane Selectivity: [wt %] | 83.3 | 87.0 |
| Average Bed Temp (° C.) | 523.5 | 551.2 |
| Inlet Propane T = 560° C. | | |
| Propane Conversion: [wt %] | 22.3 | 50.5 |
| Propane Selectivity: [wt %] | 83.8 | 87.0 |
| Average Bed Temp (° C.) | 534.3 | 561.4 |
| Inlet Propane T = 580° C. | | |
| Propane Conversion: [wt %] | 27.4 | 54.5 |
| Propane Selectivity: [wt %] | 86.7 | 87.4 |
| Average Bed Temp (° C.) | 541.9 | 572.9 |
| Inlet Propane T = 600° C. | | |
| Propane Conversion: [wt %] | 31.8 | 60.1 |
| Propane Selectivity: [wt %] | 86.3 | 85.3 |
| Average Bed Temp (° C.) | 550.0 | 579.8 |
| Temperature Profile | FIG. 1 | FIG. 2 |

EXAMPLES 3 and 4

Catalyst combinations are tested for the conversion of isobutane to isobutylene in a pseudo-adiabatic fluid bed reactor having a catalyst bed volume of approximately 75 cc. Isobutane and air are fed into the reactor through an inlet and isobutylene is recovered from an outlet. The process is carried out at a liquid hourly space velocity of −3.34, with isobutane and air temperatures from 550° C. to 590° C., and at an air to hydrocarbon ratio of 3.5 wt/wt. The reactor is operated in the cyclic mode with the cycle times of 60 seconds for reduction by hydrogen, 540 seconds for dehydrogenation, 60 seconds for nitrogen purge, 540 seconds for oxidation, and 60 seconds for nitrogen purge. The reactor is operated at atmospheric pressure during both the dehydrogenation and regeneration steps of the cycle. The cyclic operation is repeated 30 times.

EXAMPLE 3

Reactor Loading—100 vol. % catalyst combination of Example B.

EXAMPLE 4

Reactor Loading—100 vol. % catalyst combination of Example J.

TABLE 2

Performance characteristics of catalysts in isobutane dehydrogenation (Pseudo-adiabatic Fluid Bed Reactor)

|  | Example | |
| --- | --- | --- |
|  | 3 (prior art) | 4 (inventive) |
| Components (vol %) | 100% Ex. B | 100% Ex. J |
| Heat-Generating Component | none | copper oxide/ manganese oxide/ gamma-alumina |
| Inlet Isobutane T = 550° C. | | |
| Isobutane Conversion: [wt %] | 34.2 | 42.6 |
| Isobutane Selectivity: [wt %] | 89.5 | 91.2 |
| Inlet Isobutane T = 570° C. | | |
| Isobutane Conversion: [wt %] | 40.1 | 46.7 |
| Isobutane Selectivity: [wt %] | 86.6 | 90.3 |
| Inlet Isobutane T = 590° C. | | |
| Isobutane Conversion: [wt %] | 47.0 | 53.2 |
| Isobutane Selectivity: [wt %] | 84.8 | 87.5 |

EXAMPLES 5-8

Catalyst combinations are tested in an isothermal fixed bed reactor having a catalyst bed volume of approximately 30 cc for the conversion of isobutane to isobutylene. Isobutane and air are fed into the reactor through an inlet and isobutylene is recovered from an outlet. The dehydrogenation reaction is conducted at temperatures of 537° C., 567° C. and 593° C. and at a liquid hourly space velocity (LHSV) of −2/hr.

EXAMPLE 5

Reactor Loading—100 vol. % catalyst combination of Example K.

EXAMPLE 6

Reactor Loading—100 vol. % catalyst combination of Example L.

EXAMPLE 7

Reactor Loading—100 vol. % catalyst combination of Example M.

EXAMPLE 8

Reactor Loading—100 vol. % catalyst combination of Example N.

more efficient than the prior art catalyst bed that does not include a heat-generating component.

Surprisingly, as shown by the results in Table 3, when copper is combined with chromium in a dehydrogenation catalyst composition (Ex. 6), the conversion and yield from the dehydrogenation process in an isothermal unit is significantly lower than when copper is present in the catalyst bed as a component separate from but physically mixed with the chromium oxide dehydrogenation catalyst (Ex. 5). Using higher concentrations of chromium oxide and/or copper oxide (Ex. 7 and 8) does not alter these overall findings.

It is anticipated that the improved cyclic, endothermic hydrocarbon conversion process taught and claimed herein may be used in any process involving endothermic reactions

TABLE 3

Performance characteristics of catalysts in isobutane dehydrogenation
(Isothermal Fixed Bed Reactor)

| | Example | | | |
|---|---|---|---|---|
| | 5 (inventive) | 6 (comparative) | 7 (prior art) | 8 (prior art) |
| Components (vol %) | Ex. K | Ex. L | Ex. M | Ex. N |
| Heat-Generating Component | copper oxide/ α-alumina | none | none | none |
| Reaction T = 537° C. | | | | |
| Isobutane Conversion: [wt %] | 55.1 | 17.9 | 1.9 | 7.7 |
| Isobutylene Selectivity: [wt %] | 92.3 | 89.2 | 33.9 | 55.7 |
| Isobutylene Yield: [wt %] | 50.9 | 15.9 | 0.6 | 4.0 |
| Reaction T = 567° C. | | | | |
| Isobutane Conversion: [wt %] | 64.8 | 23.4 | 2.1 | 9.8 |
| Isobutylene Selectivity: [wt %] | 88.2 | 86.7 | 29.2 | 52.6 |
| Isobutylene Yield: [wt %] | 57.2 | 20.3 | 0.6 | 5.2 |
| Reaction T = 593° C. | | | | |
| Isobutane Conversion: [wt %] | 77.3 | 32.8 | 3.5 | 15.7 |
| Isobutylene Selectivity: [wt %] | 81.5 | 81.1 | 30.6 | 47.3 |
| Isobutylene Yield: [wt %] | 63.0 | 26.5 | 1.1 | 7.4 |

Figure 1:
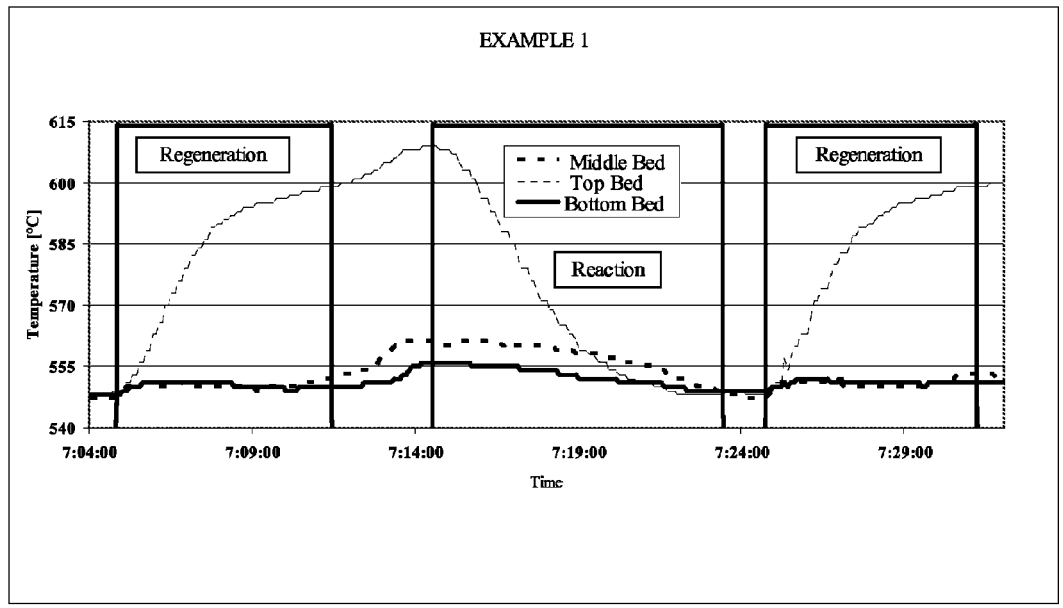
FIG. 1 is a graphical representation of the temperature profile within an adiabatic reactor loaded with 55 vol. %

FIGS. 1 and 2 show the temperature profiles in the catalyst bed for Examples 1 and 2, respectively. As demonstrated by the figures, when the heat-generating second component is included within the fixed catalyst bed during a Houdry dehydrogenation process, the catalyst bed temperature is more consistent throughout the entire bed. Without the heat-generating second component, the fluctuation in the temperature at the inlet section covers a range of about 75° C. while the fluctuation in the temperature at the outlet section covers a range of only about 5° C. Moreover, the temperature at the outlet section of the bed remains at about 560° C.—a temperature lower than desired to have optimal conversion performance from the catalyst. With the heat-generating second component, both the inlet and outlet sections of the bed experience temperature fluctuations over the course of the cyclic process of about 45° C., but the average temperature at the inlet section is about 580° C. whereas the average temperature at the outlet section is about 625° C., providing greater efficiency overall for the catalyst. As shown in Table 1, this translates to significantly higher conversion without sacrificing selectivity.

Similarly, as shown in Table 2, improvement in conversion rate is also seen when the heat-generating second component is used in fluid bed systems. Although the increase in conversion rate is not as significant in the fluid bed application as in the fixed bed application, the fluid bed application does demonstrate a directional increase in selectivity in addition to the increase in conversion indicating that the overall process is where temperature control within the catalyst bed is desired. Such processes include, but are not limited to, fixed bed paraffin dehydrogenation, fluidized bed paraffin dehydrogenation, and fluidized bed ethylbenzene dehydrogenation. In these processes, the catalyst and the catalyst combined with the heat-generating material may be layered or homogeneously mixed. Similarly, it is anticipated that the combinations of a reaction-specific catalyst combined with a heat-generating second component may be used in any process where temperature control within the catalyst bed is desired. It is understood that the composition of the catalyst and the specific processing conditions may be varied without exceeding the scope of this invention.

What is claimed is:

1. In an endothermic process that comprises contacting a hydrocarbon with a catalytic first component selected to produce a specified product mix in a catalyst bed in a fixed bed reactor, the improvement that comprises adding a heat-generating second component to the catalyst bed wherein said heat-generating component is selected so as to generate a predetermined amount of heat after being exposed to reducing reaction conditions or oxidizing reaction conditions or both reducing and oxidizing reaction conditions, wherein said heat-generating component does not promote coke formation or the formation of undesirable products under the optimal reaction conditions for the functioning of said catalytic first component, wherein said catalyst bed defines an inlet section and a middle section and an outlet section, wherein said catalytic first component is physically mixed with an inert component and loaded into said inlet section and said outlet section of said catalyst bed, and wherein said catalytic first component is physically mixed with said heat-generating second component and loaded into said middle section of said catalyst bed.

2. The process of claim 1 wherein said endothermic process consumes a predetermined amount of heat when said hydrocarbon reacts with said catalytic first component and wherein said heat-generating second component generates an amount of heat after being exposed to reducing reaction conditions or oxidizing reaction conditions or both reducing and oxidizing reaction conditions that is less than the amount of heat consumed by the reaction between said hydrocarbon and said catalytic first component.

3. The process of claim 1 wherein said endothermic process generates a temperature profile defining an average reaction temperature and a maximum catalyst bed temperature and a minimum catalyst bed temperature and wherein said temperature range for said process is defined as the maximum catalyst bed temperature minus the minimum catalyst bed temperature, and wherein said heat-generating second component is selected so as to reduce the temperature range for said endothermic process while increasing the average reaction temperature.

4. The process of claim 1 wherein said heat-generating second component comprises a metal selected from the group consisting of copper, chromium, molybdenum, vanadium, cerium, yttrium, scandium, tungsten, manganese, iron, cobalt, nickel, silver, bismuth and combinations thereof, and wherein said metal is supported on a carrier selected from the group consisting of aluminum oxides, aluminum hydroxides, aluminum trihydroxide, boehmite, pseudoboehmite, gibbsite, bayerite, transition aluminas, alpha-alumina, gamma-alumina, silica/alumina, silica, silicates, aluminates, calcium aluminate, barium hexaluminate, calcined hydrotalcites, zeolites, zinc oxide, chromium oxides, magnesium oxides and combinations thereof.

5. The process of claim 4 wherein said heat-generating second component comprises a copper compound supported on calcium aluminate.

6. An endothermic hydrocarbon conversion process that consumes a predetermined amount of heat when a hydrocarbon feed stock reacts with a catalytic first component in a catalyst bed, the process comprising:
  a) providing a multi-component catalyst bed in a fixed bed reactor comprising the catalytic first component, a heat-generating second component and an inert material, the catalyst bed having an inlet section, a middle section and an outlet section wherein a portion of the catalytic first component is physically mixed with the inert component and loaded into the inlet section and the outlet section of the catalyst bed and another portion of the catalytic first component is physically mixed with the heat-generating second component and loaded into the middle section;
  b) generating an amount of heat within the catalyst bed by exposing the heat-generating second component to reducing reaction conditions or oxidizing reaction conditions or both reducing and oxidizing reaction conditions; and
  c) reacting a hydrocarbon feed stock with the catalytic first component of the catalyst bed to form a different hydrocarbon product, wherein the heat consumed by the reaction between the hydrocarbon feed stock and the catalytic first component is supplied by the heat generated from the heat-generating material from step b).

7. The endothermic hydrocarbon conversion process of claim 6 wherein the heat generated by the heat-generating second component is less than or equal to the amount of heat consumed by the reaction between said hydrocarbon and said catalytic first component.

8. The endothermic hydrocarbon conversion process of claim 6 wherein the heat generating component does not promote coke formation or the formation of undesirable products under an optimal reaction condition for the functioning of the catalytic first component.

9. The endothermic hydrocarbon conversion process of claim 6 wherein the heat-generating second component comprises a metal at a concentration of about 2 wt % to about 40 wt % of the total heat-generating second component weight.

10. The endothermic hydrocarbon conversion process of claim 6 wherein the heat-generating second component further comprises a promoter selected from the group consisting of an alkali metal, an alkaline earth metal, lithium, sodium, potassium, rubidium, cesium, beryllium, magnesium, calcium, strontium, zirconium, barium and combinations thereof.

11. The endothermic hydrocarbon conversion process of claim 6 wherein the heat-generating second component comprises a metal selected from the group consisting of copper, chromium, molybdenum, vanadium, cerium, yttrium, scandium, tungsten, manganese, iron, cobalt, nickel, silver, bismuth and combinations thereof, and the metal is supported on a carrier selected from the group consisting of aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaluminate, calcined hydrotalcites, zeolites, zinc oxide, chromium oxides, magnesium oxides and combinations thereof.

12. The endothermic hydrocarbon conversion process of claim 6 wherein the heat-generating second component comprises a copper compound supported on a calcium aluminate carrier.

13. The endothermic hydrocarbon conversion process of claim 6 wherein the catalytic first component is a dehydrogenation catalyst, the heat-generating second component comprises a copper compound on a carrier, and the inert material is alpha-alumina.

14. The endothermic hydrocarbon conversion process of claim 6 wherein in step a), the catalytic first component is physically mixed with the heat-generating second component and the inert material.

15. The endothermic hydrocarbon conversion process of claim 6 wherein the endothermic process generates a temperature profile defining an average reaction temperature and a maximum catalyst bed temperature and a minimum catalyst bed temperature and wherein the temperature range for the process is defined as the maximum catalyst bed temperature minus the minimum catalyst bed temperature, and the heat-generating second component is selected so as to reduce the temperature range for the endothermic process while increasing the average reaction temperature.

16. The endothermic hydrocarbon conversion process of claim 6 wherein the heat-generating second component comprises a metal at a concentration of about 5 wt % to about 10 wt % of the total heat-generating second component weight.

* * * * *